United States Patent [19]

Khosravi et al.

[11] Patent Number: 5,747,273

[45] Date of Patent: May 5, 1998

[54] IMMUNOASSAY OF TOTAL INSULIN-LIKE GROWTH FACTOR BINDING PROTEIN-1

[75] Inventors: M. Javad Khosravi, Toronto, Canada; Jehangir Mistry, League City, Tex.; Anastasia Diamandi, Toronto, Canada

[73] Assignee: Diagnostic Systems Laboratories, Inc., Webster, Tex.

[21] Appl. No.: 643,830

[22] Filed: May 7, 1996

[51] Int. Cl.⁶ .................................. G01N 33/543
[52] U.S. Cl. .................. 435/7.94; 435/975; 436/510; 436/518
[58] Field of Search ................... 435/7.94, 975; 436/510, 518

[56] References Cited

U.S. PATENT DOCUMENTS

| | | | |
|---|---|---|---|
| 5,187,151 | 2/1993 | Clark et al. | 514/3 |
| 5,198,340 | 3/1993 | Makku | 435/7.8 |
| 5,212,074 | 5/1993 | Kiefer et al. | 435/69.6 |
| 5,446,024 | 8/1995 | Builder et al. | 514/12 |
| 5,554,504 | 9/1996 | Rutanen | 435/7.94 |

OTHER PUBLICATIONS

M. Westwood et al, Jour. Clin. Endocrin. Metab., 79, 1735–1744, 1994.
M. Westwood et al, Jour. Clin. Endocrinol. Metab., 80, 3520–3527, 1995.

*Primary Examiner*—David Saunders
*Attorney, Agent, or Firm*—Tamsen Valoir Jenkens & Gilchrist

[57] ABSTRACT

The present invention is for an immunoassay for the measurement of total insulin-like growth factor binding protein-1 (IGFBP-1) and is unaffected by the degree of phosphorylation of the protein. The invention is also for an immunoassay for assessing the phosphorylated variants of IGFBP-1.

17 Claims, 8 Drawing Sheets

IMMUNOASSAY OF TOTAL INSULIN-LIKE GROWTH FACTOR BINDING PROTEIN-1

BACKGROUND OF THE INVENTION

1. Field of the Invention

The present invention relates to an immunoassay for insulin-like growth factor (IGF) binder protein. More specifically, the invention relates to an immunoassay for insulin-like growth factor binding protein-1 (IGFBP-1). The total IGFBP-I method of the present invention is unaffected by the degree of phosphorylation of IGFBP-1.

2. Description of the Prior Art

Insulin-like growth factors (IGF-I and IGF-II) belong to family of peptides that mediate a broad spectrum of growth hormone-dependent as well as independent mitogenic and metabolic actions. Unlike most peptide hormones, IGFs in circulation and other physiological fluids are associated with a group of high affinity binding proteins (IGFBPs) that specifically bind and modulate their bioactivity at the cellular level. Six structurally homologous IGFBPs with distinct molecular size, hormonal control, and tissue expression and functions, have been identified (Jones JI, et al. Endocrinol Reviews 16:3–34, 1995).

IGFBP-1, synonymous with placental protein-12 and the pregnancy-associated endometrial α1-globulin, is a 25 kD protein expressed and secreted by hepatocytes, ovarian granulosa cells, and decidualized endometrium. IGFBP-1 is present in serum, it is the predominant binding protein in amniotic fluids, and is the major IGFBP in fetal and maternal circulation. Because of the reported inverse relationship between birthweight and both fetal and maternal IGFBP-1 levels, IGFBP-1 plays a critical role in fetal growth and development. In normal individuals, circulating IGFBP-1 levels fluctuate rapidly by 10-folds or more in response to the acute changes in insulin levels which has been reported to inhibit IGFBP-1 gene transcription and, thus, its production by the liver. Because of the apparent regulation of IGFBP-1 production by insulin and other glucoregulatory hormones, a significant role for IGFBP-1 in glucose counterregulation has been also proposed.

IGFBP-1 is capable of both inhibition as well as augmentation of the IGFs' actions. These observations may be explained by the findings that differential phosphorylation of IGFBP-1 could significantly alter its affinity for the IGFs and, therefore, its capacity to influence their cellular responsiveness. Analysis of IGFBP-1 by anion exchange chromatography and non-denaturing polyacrylamide gel electrophoresis has identified up to five IGFBP-I variants, differing only in their degree of phosphorylation. Various cell types such as Hep G2, decidual and liver cells have been found to secrete predominantly phosphorylated forms, whereas amniotic fluid and fetal serum contain substantial amounts of non and lesser phosphorylated variants (Jones JI, et al. Endocrinol Reviews 16:3–34, 1995). In contrast, in the sera of normal adults only a single highly phosphorylated variant of IGFBP-1 has been detected (Westwood M, et al. J Clin Endocrinol Metab 80:3520–27, 1995). The IGFBP-1 profile of normal adult serum may, however, change under certain conditions such as during pregnancy or in subjects with Laron's syndrome (LS) when non and lesser phosphorylated variants are also expressed (Westwood M, et al. J Clin Endocrin Metab 79:1735–1741, 1994). Dephosphorylation of IGFBP-1 has been proposed as a possible mechanism for increasing IGF bioavailability (Westwood M, et al. J Clin Endocrinol Metab 79:1735–1741, 1994). This conclusion may be warranted as the non-phosphorylated IGFBP-1 isoforms have reportedly 4- to 6-fold lower binding affinity for IGF-1 as compared to the phosphorylated variants (Jones JI, et al. Proc Natl Acad Sci USA 88:7481–7485, 1991). The stimulation and inhibition of the IGF actions have been found in association with the non-phosphorylated and phosphorylated IGFBP-1 variants, respectively.

Changes in the phosphorylation states of IGFBP-1 has also been reported to result in a significant change in its immunoreactivity. As a result of differential recognition of the various IGFBP-1 phosphoforms by two different antibodies, up to 11-fold differences in the circulating IGFBP-1 levels have been observed (Westwood M, et al. J Clin Endocrinol Metab 79:1735–1741, 1994). The above observations have been primarily made with immunoprecipitation followed by non-denatured gel electrophoresis and Western ligand blotting with [$^{125}$I]IGF-1 which are difficult to routinely perform on a large number of patients. As a consequence, rapid progress in this area has been hampered by unavailability of simple and reliable immunoassay methods and kits for precise quantification of the total levels as well as the IGFBP-1 subfractions or ratios. Because variable antibody recognition of the IGFBP-1 isoforms may result in false estimates of its actual levels, development of immunoassays unaffected by the state of IGFBP-1 phosphorylation is urgently needed. There has not heretofore been an immunoassay which accurately assesses IGFBP-1 without regard to its phosphorylation.

SUMMARY OF THE INVENTION

In accordance with the present invention, provided herein is an immunoassay method for the detection of total insulin-like growth factor binding protein-i in a fluid comprising the steps of: contacting a sample of fluid suspected of containing insulin-like growth factor binding protein- I with a first capture antibody that binds to total insulin-like growth factor binding protein-1 to form a complex, wherein said first capture antibody is unaffected by the degree of phosphorylation of insulin-like growth factor binding protein-1, and wherein said first capture antibody is bound to a solid carrier, said solid carrier being insoluble in said fluid; contacting the complex with a second detecting antibody, wherein said second detecting antibody is unaffected by the degree of phosphorylation of insulin-like growth factor binding protein-1 and wherein said second detecting antibody is labeled; separating said solid carrier from said fluid sample and unreacted second detecting antibody; measuring either the amount of labeled second detecting antibody associated with the solid carrier or the amount of unreacted labeled second detecting antibody; and relating the amount of labeled antibody measured with the amount of labeled antibody measured for a control sample prepared in accordance with steps (a)–(d), said control sample being known to be free of insulin-like growth factor binding protein, to determine the presence of total insulin-like growth factor binding protein in said fluid sample, or relating the amount of labeled antibody measured with the amount of labeled antibody measured for samples containing known amounts of insulin-like growth factor binding protein prepared in accordance with steps (a)–(d) to determine the concentration of total insulin-like growth factor binding protein in said fluid sample.

Also, provided herein is an immunoassay method for the detection of phosphorylated insulin-like growth factor binding protein- 1 in a fluid comprising the steps of: contacting a sample of fluid suspected of containing insulin-like growth factor binding protein-1 with a first capture antibody that binds to total insulin-like growth factor binding protein-1 to form a complex, wherein said first capture antibody is unaffected by the degree of phosphorylation of insulin-like growth factor binding protein-1, and wherein said first capture antibody is bound to a solid carrier, said solid carrier being insoluble in said fluid; contacting the complex with a second detecting antibody, wherein said second detecting antibody is unaffected by the degree of phosphorylation of insulin-like growth factor binding protein- 1 and wherein said second detecting antibody is labeled; separating said solid carrier from said fluid sample and unreacted second detecting antibody; measuring either the amount of labeled second detecting antibody associated with the solid carrier or the amount of unreacted labeled second detecting antibody; relating the amount of labeled antibody measured with the amount of labeled antibody measured for a control sample prepared in accordance with steps (a)–(d), said control sample being known to be free of insulin-like growth factor binding protein, to determine the presence of total insulin-like growth factor binding protein in said fluid sample, or relating the amount of labeled antibody measured with the amount of labeled antibody measured for samples containing known amounts of insulin-like growth factor binding protein prepared in accordance with steps (a)–(d) to determine the concentration of total insulin-like growth factor binding protein in said fluid sample; contacting the complex with a third detecting antibody wherein said third detecting antibody binds to non-phosphorylated insulin-like growth factor binding protein-1 and wherein said third detecting antibody is labeled; separating said solid carrier from said fluid sample and unreacted third detecting antibody; measuring either the amount of labeled third detecting antibody associated with the solid carrier or the amount of unreacted labeled third detecting antibody; relating the amount of labeled antibody measured with the amount of labeled antibody measured for a control sample prepared in accordance with steps (f)–(g), said control sample being known to be free of said non-phosphorylated insulin-like growth factor binding protein, to determine the presence of non-phosphorylated insulin-like growth factor binding protein in said fluid sample, or relating the amount of labeled antibody measured with the amount of labeled antibody measured for samples containing known amounts of non-phosphorylated insulin-like growth factor binding protein prepared in accordance with steps (f)–(g) to determine the concentration of non-phosphorylated insulin-like growth factor binding protein in said fluid sample; and calculating the difference between the total insulin-like growth factor binding protein- 1 concentration as determined in step (e) and the non-phosphorylated insulin-like growth factor binding protein as determined in step (i) to derive the concentration of phosphorylated insulin-like growth factor binding protein-1.

Additionally, also provided herein is a kit for measuring total insulin-like growth factor binding protein-1 comprising a first capture antibody that binds to insulin-like growth factor binding protein-1, wherein said first capture antibody is unaffected by the degree of phosphorylation of insulin-like growth factor binding protein-1, and a second detecting antibody, wherein said second detecting antibody is unaffected by the degree of phosphorylation of insulin-like growth factor binding protein-1.

These and other advantages of the present invention will become apparent from the following detailed description.

BRIEF DESCRIPTION OF THE DRAWINGS

FIG. 3. Serum IGFBP-1 in Relation to Glucose Intake. FIG. 3A, normal female. FIG. 3B, normal male. Closed squares represent ELISA-1, open squares ELISA-2, and triangles ELISA-3.

FIG. 4. Comparison of ELISA-1 with ELISA-2 (FIG. 4A) and ELISA -3 (FIG) 4B).

FIG. 7. IGFBP-1 in AF and CSF Before (FIG. 7A) and After (FIG. 7B) Dephosphorylation. Open bars represent ELISA-1, blackened bars represent ELISA-2, and hatched bars represent ELISA-3.

DETAILED DESCRIPTION OF THE INVENTION

The present invention describes antibodies that bind to IGFBP-1. These antibodies are useful in immunoassays for the measurement of IGFBP-1. As would be appreciated by one skilled in the art, the antibodies of the present invention may be polyclonal or monoclonal.

The antibodies of the present invention are useful in measuring total IGFBP-1 the non-phosphorylated variants of IGFBP- 1, and/or the phosphorylated variants of IGFBP-1. As would be appreciated by one skilled in the art, ratios of these fractions are also useful. For example, the measurement of the total IGFBP-1 levels or the ratios outlined above could be used in assessing hormonal regulation of the IGFBP-1 phosphorylation/dephosphorylation which appears to be involved in the IGFBP-1 regulation of the IGFs' actions. Elucidation of this mechanism may lead to identification of new functions or clinical usage for IGFBP- 1 under the physiological or abnormal conditions where changes in total levels or phosphorylation status of IGFBP-1 might be suspected. For example, there are currently recent examples of changes in the levels of IGFBP-1 in association with birthweight as well as changes in the circulating IGFBP-1 profile in conditions such as during pregnancy, in patients with Laron's syndrome and insulin-dependent diabetes mellitus (Westwood et al. J Clin Endocrinol Metab 80:3520–27, 1995). These assays are useful in evaluating and monitoring fetal growth and development, pregnancy and its related conditions. As used herein, an alternative embodiment of the present invention employs the measurement of the ratio of non-phosphorylated IGFBP-1 to total IGFBP-1, or the ratio of phosphorylated IGFBP-1 to total IGFBP-1.

The anti-IGFBP-1 polyclonal antibodies of the present invention may be raised against IGFBP-1 purified form human amniotic fluids by published methods (Powell, DR et al. J Biol Chem 1991; 266:18868–76, incorporated by reference herein). The antibody may be raised from amniotic fluid in goats using standard immunization and bleeding procedures, although any other convenient vertebrate sources such as murine, primate, bovine, ovine, equine, porcine, sheep, etc. may be employed. Animal bleeds with high antibody titers may be fractionated by routine selective salting-out procedures such as antibody precipitation with ammonium sulphate. The specific immunoglobulin fraction of the serum may be finally separated by affinity chromatography purification on IGFBP-1-Sepharose column prepare according to standard laboratory methods. The purified antibody must be then characterized for lack of cross-reactivity with related molecules such as IGFBP-2–6 as well as IGF-I, IGF-II and insulin. This could be easily performed by standard methods using labeled IGFBP-1 (e.g. with radioisotopes such as, but not limited to $^{125}$I) as tracer in competition with increasing levels of unlabeled cross-reactants for antibody binding. If significant cross-reactivity with any of the potential cross-reactant occurred at their respective physiological/non-physiological levels, then further purification of the antibody on affinity columns made by coupling the particular cross-reactant to activated Sepharose column should be performed and the purified antibody re-tested as above. In some instances, it may be necessary to evaluate the purity of the immunogen and if a relatively unpure preparation was used, re-immunize the animal with a highly IGFBP-1 enriched preparation. Evaluation of cross-reactivity should be also performed with the monoclonal IGFBP-1 antibodies, and those demonstrating unacceptable levels or abnormal responses should be rejected.

In addition to cross-reactivity studies, both polyclonal and monoclonal antibodies should be tested for potential interference with IGFs binding to IGFBP-1. As exemplified in Table 1, this could be performed either in an ELISA format, or by direct coating of each of the antibody to a solid support and evaluating their binding to labeled IGFBP-1 (e.g. with $^{125}$I or other radiolabels) before and after preincubation (e.g. for 2 hr at room temperature) with increasing levels of IGF-I or IGF-II. Antibodies which bind to antigenic determinants at or near the ligand (IGF-I or IGF-II) binding site of IGFBP-1 will demonstrate significantly reduced binding to the labeled IGFBP-1 which has been pre-incubated with the ligand. Other techniques known to those skilled in the art may also be used.

Figure 5:
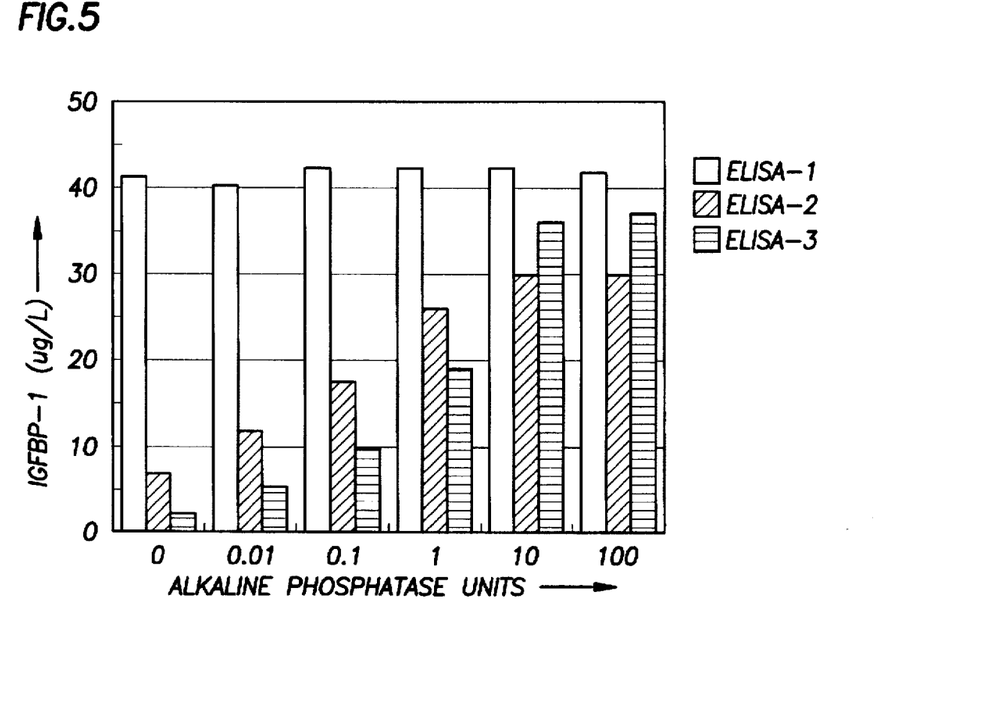
FIG. 5. Effect of IGFBP-1 Dephosphorylation on ELISA-1-3. Open bars represent ELISA-1, blackened bars represent ELISA-2, and hatched bars represent ELISA-3.

Both the monoclonal and polyclonal IGFBP-1 antibodies may be individually evaluated for their binding to phosphorylated and unphosphorylated IGFBP-1. This could be performed by coating the antibodies onto a solid-support and evaluating their binding to labeled (e.g. with radiolabeled such as, but not limited to $^{125}$I) phosphorylated IGFBP-1 (e.g. IGFBP-1 purified from serum using published methods) before and after pre-treatment with alkaline phosphatase (ALP) which is known to readily dephosphorylate IGFBP-1. Antibodies that are unaffected by phosphorylation detect little or no change in IGFBP-1 binding in response to ALP treatment, while those affected by phosphorylation will demonstrate an obvious increase or decrease in signal (relative to the untreated sample), depending on whether it preferentially recognized the non-phosphorylated or phosphorlated variants of IGFBP-1, respectively. Alternatively, if an antibody that is unaffected by IGFBP-1 phosphorylation is identified, then it could be used as a coating antibody paired with other labeled IGFBP-1 antibodies for detecting serum IGFBP-1 in response to pre-treatment with increasing concentrations of ALP. Antibodies that are unaffected by phosphorylation demonstrate no significant change in IGFBP-1 levels detected (i.e. phosphorylation-insensitive). Antibodies that recognize primarily non-phosphorylated FBP-1 variants will measure a fraction of IGFBP-1 detected by the phosphorylation-insensitive antibody, but show a steady increase in signal relative to increasing ALP treatment as shown in FIG. 5. The most specific antibodies for the non-phosphorylated IGFBP-1 detects the lowest concentration in ALP-untreated normal adult serum (which contains primarily a single highly phosphorylated species), but measures values within $\geq 80\%$ of those detected by the phosphorylation-insensitive antibody in ALP-treated serum samples (see FIG. 5). Conversely, antibodies with preferred binding for the phosphorylated variants may measure high levels in the untreated samples (could be even higher than the levels measured by the phosphorylation-insensitive antibody), but demonstrate sharp decreases in response to ALP treatment. Other techniques known to those skilled in the art such may also be used to establish relative antibody specificity. Alternatively, it is also possible to develop antibodies with defined specificity based on the recombinant gene technology. In an alternative embodiment chimeric antibodies may be developed and used.

Monoclonal antibodies may prepared according to the well established standard laboratory procedures "Practice and Theory of Enzyme Immunoassays" by P. Tijssen (In Laboratory Techniques in Biochemistry and Molecular Biology, Eds: R.H. Burdon and P.H. van Knippenberg; Elsevier Publishers Biomedical Division, 1985) which are based on the original technique of Kohler and Milstein (Kohler G. Milstein C. Nature 256: 495, 1975). This is usually performed by removing spleen cells from immunized animals and immortalizing the antibody producing cells by fusion with myeloma cells or by Epstein-Bar virus transformation, and then screening for clones expressing the desired antibody, although other techniques known to those skilled in the art may also be used.

The antibody used for detecting the antigen bound to the solid-phase antibody may be either directly labeled or detected indirectly by a secondary detection system. The latter may be based on the principle of antibody recognition by a labeled anti-species antibody or any form of other immunological or non-immunological bridging detection systems, e.g., the biotinstrept(avidin) technology.

The label used for direct or indirect antibody labeling may be any detectable reporter molecule. Examples of suitable labels are those widely used in the field of immunological or non-immunological detection systems, and may include moieties that could be detected directly, such as fluorophores, luminescent, metal complexes and radioactive labels, as well as moieties that could be detected by other suitable reagents such as enzymes or various combinations of direct or indirect labels such as enzymatic with luminometric substrates. Examples of such labels may include all varieties of radioisotopes such as, but not limited to $^{125}$I, $^{131}$I, $^{32}$P, $^{14}$C, and $^{3}$H, and combinations thereof. In an alternative embodiment, labels may include enzymes such as alkaline-phosphatase, amylases, luciferases, catalases, beta-galactosidases, glucose oxidases, glucose-6-phosphate dehydrogenases, hexokinases, horseradish peroxides, lactamases, ureases and malate dehydrogenases, and combinations thereof. Fluorophores include, but are not limited to coumarines, rare earth metal ions and/or their chelates or chelate complexes, fluorescein, rhodamines and their derivatives. Metal complexes such as carbonyl complexes and their derivatives, stable free radical, vesicles (liposomes), colloidal particles, latex particle, spin labels, biotin/avidin and their derivatives and modifications could be also used.

The antibodies of the present invention find use in diagnostic assays for the determination of IGFBP. The antibodies of the invention may be used in most assays involving antigen-antibody reactions. The assays may be homogeneous or heterogeneous. In a homogeneous assay approach, the sample can be a biological fluid such as serum, urine, whole blood, lymphatic fluid, plasma, saliva, and the like, cerebrospinal fluid, amniotic fluid, cells, tissue, and material secreted by cells or tissues cultured in vitro. The sample can be pretreated if necessary to remove unwanted materials. The immunological reaction usually involves the specific antibody, labeled analyte, and the sample suspected of containing the analyte. The analyte can be directly labeled with the label or indirectly labeled with a means for incorporating the label such as conjugation of the analyte to biotin and having labeled avidin or anti-biotin. The signal from the label is modified, directly or indirectly, upon the binding of the antibody of the labeled analyte. Both the immunological reaction and detection of the extent thereof are carried out in a homogeneous solution. Labels which may be employed as part of a signal producing system capable of producing a signal in relation to the amount of analyte in the sample include free radicals, chromogens, such as fluorescent dyes, chemiluminescers, enzymes, bacteriophages, coenzymes particulate labels and so forth.

In a heterogeneous assay approach, the reagents are usually the sample, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal or signal producing system. The signal is related to the presence of the analyte in the sample. Means for producing a detectable signal includes the use of radioactive labels, fluorescers, enzymes, and so forth. Examples of heterogeneous immunoassays are the radioimmunoassay, immunofluoroescence methods, enzyme-linked immunoassays, and the like.

The assay for total insulin-like growth factor binding protein-1, non-phosphorylated and phosphorylated insulin-like growth factor binding protein-1 is preferably a non-competitive assay, although a competitive assay may be used as well.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817, 837; 3,850,578; 3,853,987; 3,867,517; 3,901,654; 3,935, 074; 3,984,533; 3,996,345; and 4,098,876, which listing is not intended to be exhaustive.

The binding of the antibody of the invention to the surface may be accomplished by well known techniques, commonly available in the literature. See, for example, "Immobilized Enzymes," Ichiro Chibata, Halstad Press, New York (1978) and Cuatrecasas, J. Bio. Chem., 245: 3059 (1970).

In carrying out the assay in accordance with this embodiment of the invention the sample is mixed with an aqueous medium and the medium is contacted with the surface having an antibody of the invention bound thereto. Members of a signal producing system and any ancillary materials may also be included in the aqueous medium, either concurrently or added subsequently so as to provide a detectable signal associated with the surface. The means for producing the detectable signal can involve the incorporation in the medium of a labeled analyte or it may involve the use of a second antibody having a label conjugated thereto. Separation and washing steps will be carried out as needed. The signal detected is related to the presence of IGFBP-1 in the sample. It is within the scope of the present invention to include a calibration as well as the measurement surface on the same support.

In a preferred embodiment of the present invention, monoclonal antibody to IGFBP-1 is used as a coating antibody. The coating antibody is unaffected by the degree of phosphorylation of IGFBP-1. The coating monoclonal antibody is available, for example from Diagnostic Systems Laboratories, Inc., Webster, Tex., U.S.A. Alternatively, a polyclonal antibody may be used as the coating antibody. This polyclonal coating antibody must be unaffected by the degree of phosphorylation of IGFBP-1. The detecting antibody of the present invention must likewise be unaffected by the degree of phosphorylation of IGFBP-1. The detecting antibody is preferably polyclonal, but may be monoclonal as well. Alternatively, non-phosphorylated variants of IGFBP-1 may be detected using the coating or capture antibody described above, and a detecting monoclonal antibody such as is available from Medix Biochemica, Kauniainen, Finland. In yet another embodiment, the total IGFBP-1 and non-phosphorylated variant assay may be conducted sequentially, and the amount of phosphorylated IGFBP-1 calculated from the difference between the total and non-phosphorylated values.

The invention also includes kits, e.g., diagnostic assay kits, for carrying out the methods disclosed above. In one embodiment, the kit comprises in packaged combination a capture or coating antibody more specifically defined above, and a detecting antibody. The kit may also include reagents such as buffering agents and protein stabilizing agents, e.g., polysaccharides and the like. The kit may further include, where necessary, other members of the signal producing system of which system the label is a member, agents for reducing background interference in a test, control reagents, standards, apparatus for conducting a test, and the like.

We report for the first time development and performance characteristics of a novel non-competitive ELISA for total IGFBP-1 that is unaffected by changes in its states of phosphorylation. The distinguishing feature of the assay has been established by showing that the measured IGFBP-1 levels in various biological fluids remains virtually unchanged after sample pre-treatment with alkaline phosphatase which is known to readily dephosphorylate IGFBP-1 (Frost RA, et al. J Biol Chem 266:18082–18088, 1991). Comparison of the present total IGFBP-1 ELISA (ELISA-1) with other ELISAs (ELISA-2 and ELISA-3) that measure a subset of non or lesser IGFBP-1 phosphoforms and a commercially available IGFBP-1 IRMA is also presented. As used herein, ELISA-1 measures total IGFBP-1, ELISA-2 and ELISA-3 measure non-phosphorylated IGFBP-1.

The following examples serve to illustrate specific embodiments of the invention, but should not be considered as a limitation on the scope of the invention.

Example 1: IGFBP-1 Immunoassay

Recombinant human IGF-I and IGF-II were obtained from GroPep, Pty, Ltd., Adelaide, Australia (distributed by DSL, Inc., Webster, Tex.) and recombinant non-glycosylated IGFBP-3, was obtained from Celtrix Pharmaceuticals, Inc., Santa Clara, Calif. Recombinant human IGFBP-2, and IGFBP-4–6 were purchased from Austral Biologicals, San Roman, Calif. IGFBP-1 was purified from human amniotic fluid according to previously described methods (Powell, DR et al. J Biol Chem 1991; 266:18868–76).

The IGFBP-1 assay buffer was 0.05 mol/L Tris-maleate, pH 7.0, 9 g/L NaCl, 20 g/L bovine serum albumin (BSA), 0.1 g/L thimerosal. The antibody-HRP conjugate buffer was 0.02 mol/L sodium phosphate, pH 7.0, 9 g/L NaCl, 1 g/L $CaCl_2$, 5 g/L BSA, 0.1 g/L thimerosal. The stopping solution was 2 mol/L sulphuric acid in deionized water. The composition of the coating and blocking buffers as well as the wash solution were as described previously (Khosravi, MJ et al. Clin Chem 1991; 37:58–63).

IGFBP-1 antibody coating to microtiter wells was performed at a concentration of 0.25–20 mg/L using previously published methods (Khosravi et al. Clin Chem 37:58–63, 1991). In brief, 0.1 mL of the capture antibody solution was added to each microwell and allowed to incubate overnight at room temperature. The wells were then washed X1 with the wash solution and 0.2 mL/well of the blocking solution was added and allowed to incubate for 1 hr as above. The wells were washed X1 prior to use.

The IGFBP-1 detection antibodies were coupled to HRP as previously described (Khosravi, MJ et al. Clin Biochem 1995; 28:407–14). The coupling reaction involved activation of the enzyme with sulfo-SMCC and its subsequent conjugation to the anti-IGFBP-1 detection antibody which had been activated by 2-iminothiolane. The stock HRP-conjugated antibody solution was diluted at least 1000-fold prior to use.

IGFBP-1 standards were prepared by dissolving IGFBP-1 from amniotic fluid in a protein-based buffer matrix (0.05 mol/L sodium phosphate, pH 7.4, 5 g NaCl, 1 g/L BSA, 0.1 g/L thimerosal) or in newborn calf serum (NBCS) containing 0.1 g/L thimerosal. Standards were then calibrated against pure human IGFBP-1 from amniotic fluid, and diluted in the standard matrix to give IGFBP-1 standard values of ~0.5, 1.0, 2.0, 10, 40, 80, and 160 µg/L. The standards were stable for up to 4 weeks at 4° C. and >6 months at −20° C. or lower. IGFBP-1 quality control samples were either human serum samples containing various levels of endogenous IGFBP-1 or prepared by spiking the zero standard of the assay with different levels of IGFBP-1. The nominal concentrations of the control samples were established by analyzing them in the IGFBP-1 ELISA.

The IGFBP-1 ELISA was performed according to previously described procedures after determination of optimal assay conditions (Khosravi, MJ et al. Clin Chem 1987; 33:1994–9). Standards or samples (0.025 mL) were added in duplicate to the pre-coated wells, followed by addition of the assay buffer (0.05 mL) and 1 hr incubation at room temperature with continuous shaking. The wells were washed X4 and incubated with 0.1 mL/well of the appropriate anti-IGFBP-1 antibody-HRP conjugate (diluted in the assay buffer to approximately 0.1–0.25 mg/L) for 30 min at room temperature. The wells were washed X5 with the wash solution and 0.1 mL of the $TMB/H_2O_2$ substrate solution was added for an additional 10 min incubation at room temperature. Stopping solution (0.1 mL) was then added and absorbance is measured by dual wavelength measurement at 450 nm with background wavelength correction set at 620 nm. Optical density measurements for all ELISAs were performed with the Labsystems Multiskan Multisoft microplate reader (Labsystems, Kauniainen, Finland).

The best standard curve characteristics were obtained with a coating monoclonal antibody paired with a polyclonal (ELISA-1) or three of the remaining four monoclonal antibodies (ELISA-2-4) used for detection. The detection monoclonal antibodies were from Medix Biochemica, Kauniainen, Finland. We assumed that the monoclonal antibody that did not paired with the coating antibody was recognizing identical or closely related epitope(s) on the IGFBP-1 molecules.

Because of the possible antibody recognition of antigenic determinants at or near the ligand (IGF-I or IGF-II) binding site of IGFBP-1, ELISA-1–4 were tested for potential interferences by free IGFs. As shown in Table 1, IGF-1 at concentrations up to 200 µg/L added to a buffer-based IGFBP-1 preparation (~8 µg/L) did not interfere with IGFBP-1 measured by ELISA-1, but showed some interferences in ELISA-3 at relatively high levels (>50 µg./L). In contrast, ELISA-2 showed significant interferences by free IGF-1 at levels >5 µg/L, and ELISA-4 falsely overestimate the expected IGFBP-1 levels and was therefore discontinued. In ELISA-2, the interfering effects of the free IGF-1 added to actual serum samples occurred at a significantly higher concentrations (>10 µg/L). As this level of free IGFs may be well above the expected endogenous levels available for binding to IGFBP-1, ELISA-2 was further evaluated.

TABLE 1

IGFBP-1 ELISA Binding Interference with IGF-I

| IGF-I added, | IGFBP-1 Measured, µg/L* | | | |
|---|---|---|---|---|
| µg/L | ELISA-1 | ELISA-2 | ELISA-3 | ELISA-4 |
| 0 | 7.3 | 7.2 | 7.6 | 7.7 |
| 5 | 7.4 | 5.3 | 7.3 | NT |
| 50 | 7.8 | 1.9 | 6.2 | 19.6 |
| 200 | 7.8 | 1.3 | 6.0 | 22.0 |

*Expected IGFBP-1 concentration = 8.0 µg/L
NT = Not tested

The IGFBP-1 ELISA protocols were optimized for analytical performance before further evaluation. This was easily achievable as the ELISA-1–3 are based on a common monoclonal capture antibody and a two-step immunoassay protocol which allows detection of the bound IGFBP-1 by each of the three different detection antibody in a separate step (i.e. the second step). These characteristics were advantages as they also allowed employment of a common ELISA-1-3 protocol.

The protocol optimization was based on the initial evaluation of a number of factors that could potentially effect performance with regard to detection limit, dynamic range, precision and delayed sample addition. The best performances were obtained with a coating antibody concentration of 5 mg/L (500 ng/0. 1 mL/well), a detection antibody concentration of ~0.1–0.25 mg/L (10–25 ng/0.1 mL/well), a sample size of 0.02 mL/well, a first and second step room temperature incubations of 60 and 30 min, respectively, and a 10 min substrate development step. With this protocol, the differences in assay results caused by 1–20 min delay between addition of the same samples into the coated wells was <10%.

Figure 1:
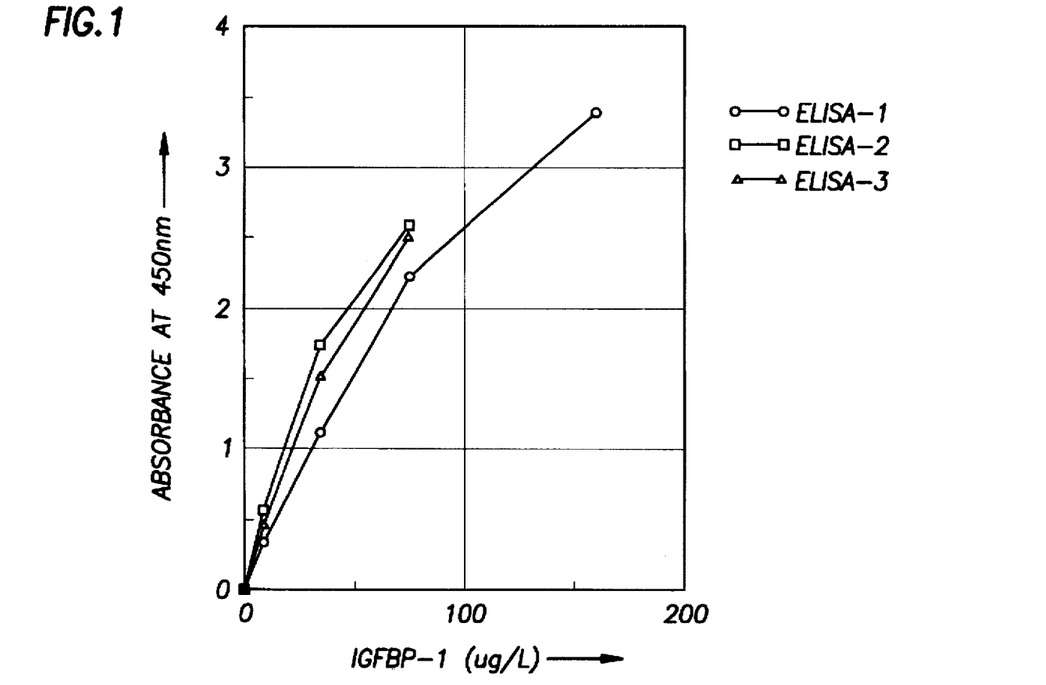
FIG. 1. IGFBP-1 ELISA-1-3: Typical Standard Curves. Closed squares represent ELISA-1, open squares ELISA-2, and triangles ELISA-3.

A typical standard curve for ELISA-1-3 is shown in FIG. 1, and the performance characteristics of the assays is summarized in Table 2. The lower limit of detection (sensitivity) was determined by interpolating the mean plus 2SD of 12 replicate measurements of the zero standard. The intra-assay CVs were determined by replicate analysis (n=12) of 4 samples in one run and interassay CVs by duplicate measurement of the samples in 9–12 separate assays at IGFBP-1 levels of ~3–50 µg/L. Recovery was assessed by adding 25 uL of exogenous IGFBP-1 diluted in the standard matrix to 225 uL of three serum samples and analyzing the spiked and unspiked samples in ELISA- 1–3. Percent recovery was determined by comparison of the amount of added IGFBP-1 to the amount measured after subtracting the endogenous levels. Linearity was tested by analyzing three serum samples after serially diluted (2–32 fold) with the zero standard of the assay.

TABLE 2

IGFBP-1 ELISA Validation Data

| Assay parameter | ELISA-1 | ELISA-2 | ELISA-3 |
|---|---|---|---|
| Detection limit (µg/L) | 0.30 | 0.12 | 0.07 |
| Standard range (µg/L) | 1–180 | 0.45–80 | 0.45–80 |
| Intrassay CV (%) | 2.9–5.8 | 2.2–5.3 | 3.3–5.3 |
| Interassay CV (%) | 5.4–8.4 | 5.9–7.4 | 4.5–5.6 |
| Recovery of added IGFBP-1 (%) | 92 ± 5.1 | 92 ± 3.2 | 91 ± 6.2 |
| Recovery after dilution (%) | 106 ± 6.1 | 87 ± 7.5 | 90 ± 8.6 |

Analysis of IGFBP-2 and IGFBP-4–6 (up to 500 µg/L), IGFBP-3 (up to 4.2 mg/L) and insulin (up to 200 µg/L) added to the zero standard or a standard preparation of ~8 µg of IGFBP-1/L did not show any cross-reactivity or interferences in IGFBP-1 ELISA -1–3. Direct addition of IGF-1 (up to 200 µg/L), IGF-II (up to 120 µg/L) to the assay zero standard followed by IGFBP-1 analysis by ELISA-1–3 did not show any cross-reactivity.

Example 2: Immunoreactivity Characteristics

Figure 2:
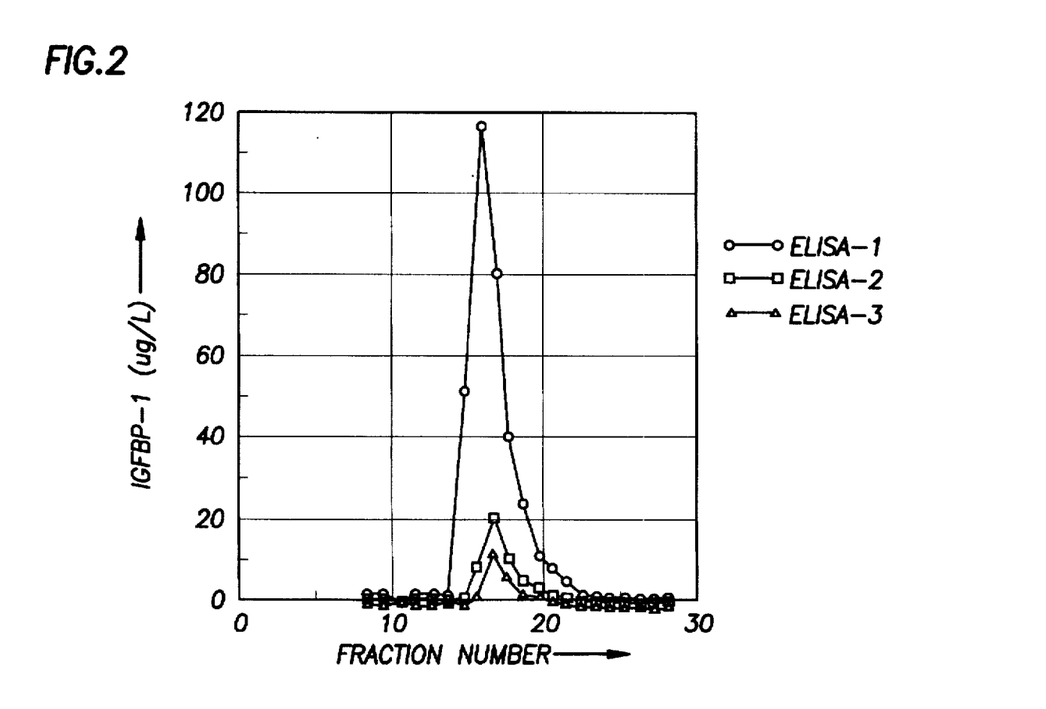
FIG. 2. HPLC Profile of Immunoreactive IGFBP-1. Closed squares represent ELISA-1, open squares ELISA-2, and triangles ELISA-3.

To study distribution of the immunoreactive substances in serum, 0.2 mL of a fresh serum was subjected to size-exclusion chromatography on a precalibrated 600×7.5 mm Bio-Sil SEC-250 HPLC column (Bio-Rad) as described (Khosravi, MJ et al. Clin Biochem 1995;28:407–14). The column was pre-equilibrated and eluted with 0.05 mol/L Tris HCl, pH 7.2, 9.0 g/L NaCl at 0.5 mL/min with collection of 1.0 mL fractions. Distribution of IGFBP-I immunoreactivity was determined by assaying each fraction for IGFBP-1 by ELISA-1–3. The column was calibrated with molecular weight standards from BioRad Laboratories eluting at fraction 9 (660 kDa), 12 (160 kDa), 15 (44 kDa), 17 (17 kDa) and 21 (1.4 kDa). As expected, a major peak at ~30 kD, corresponding to the reported molecular weight of IGFBP-1 (Lee, PKD et al. Proc Soc Exp Biol Med 204:4–29, 1993), was detected by ELISA-1–3 . However, there appear to be significant differences in the peak IGFBP-1 intensity measured by the three methods (FIG. 2).

Example 3: Physiological Investigations

Figure 3A:
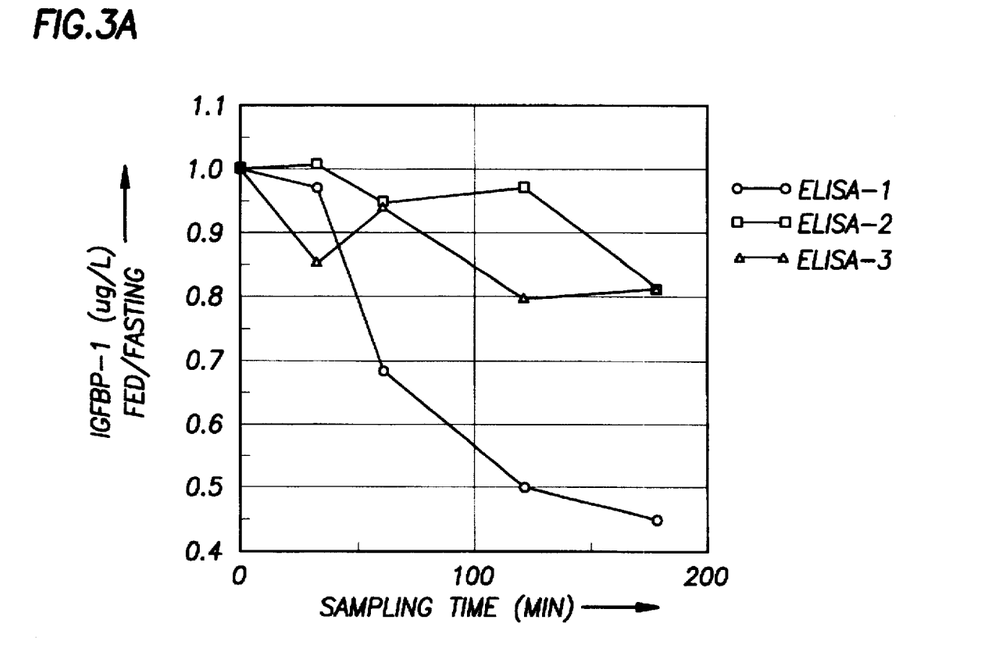
Figure 3B:
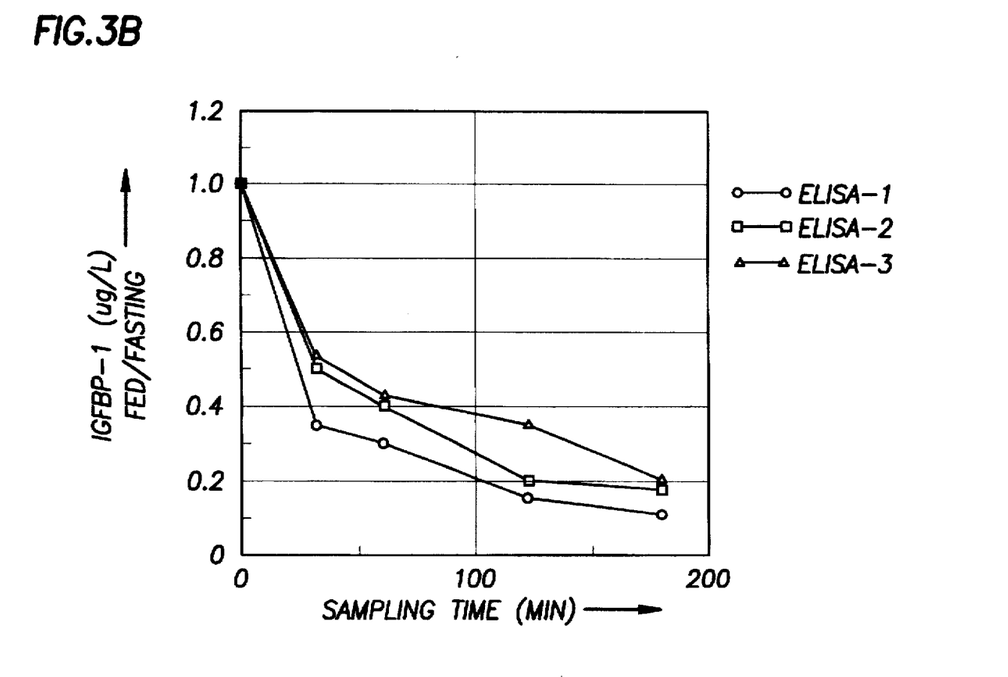

It is now well established that production of IGFBP-1 by the liver is inversely regulated by insulin so that in normal individuals, serum IGFBP-1 should fall rapidly after a meal, while increases should occur during fasting (Lee, PDK et al. Proc Soc Exp Biol Med 204:4–29, 1993). To evaluate the assay response to meal-induced IGFBP-1 suppression, timed serum samples taken from two apparently normal individuals during glucose tolerance (75 gram) testing were assayed. As shown in FIG. 3, the expected post-meal decline in IGFBP-1 was clearly registered by ELISA-1–3, further confirming the specificity of the assays for IGFBP-1. However, in another sample, only ELISA-1 was able to demonstrate decreasing IGFBP-1 levels. The responses of ELISA-2 and ELISA-3 were relatively flat and blunted which may be related to changes in the phosphorylation status of circulating IGFBP-1 (see below).

Figure 4A:
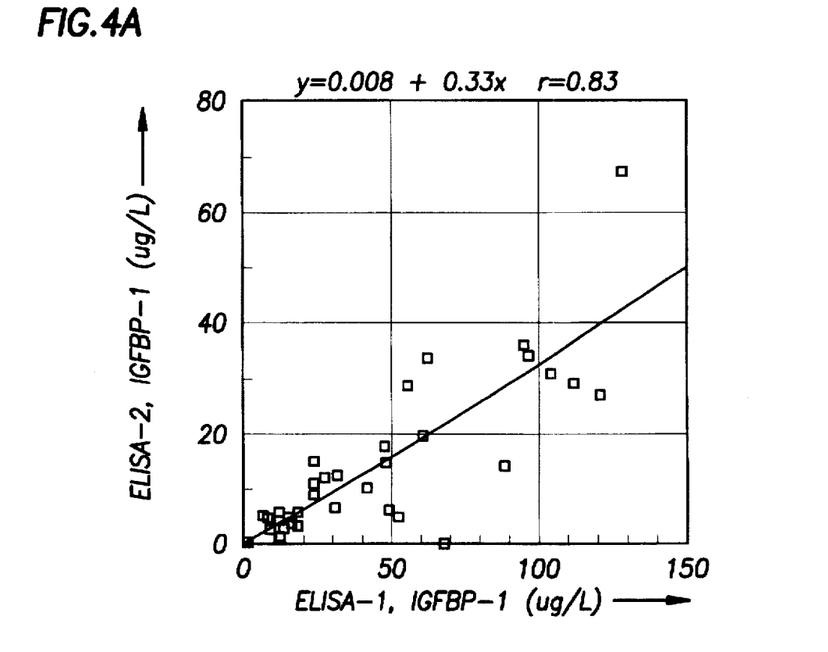
Figure 4B:
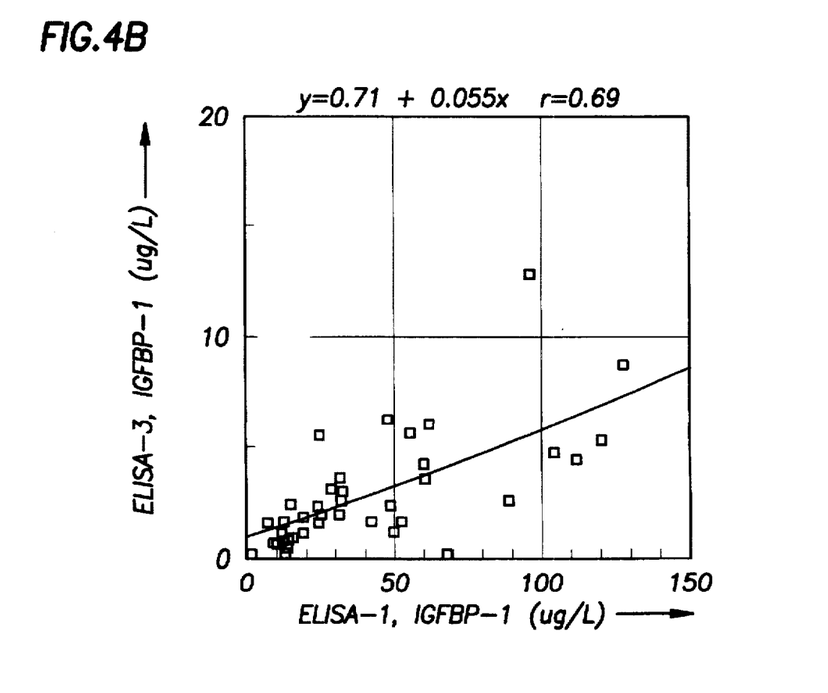

The IGFBP-1 ELISA-1–3 measured considerably different concentrations in randomly selected serum samples (n=44) and synovial fluids (SF, n=6) (Table 3 ). The median serum value measured by ELISA-1 was 3.3- and 13.0-fold higher than the levels measured by ELISA-2 and ELISA-3, respectively. Furthermore, regression analysis of values by ELISA-2 and −3 showed a relatively poor correlations in comparison to ELISA-1 with significant scattering of data points around the regression line (FIG. 4). In FIG. 4A, ELISA- I and ELISA-2 are shown. In FIG. 4B, ELISA-1 and ELISA-3 are shown. The median IGFBP-1 levels by ELISA-1–3 in SF were 19.2, 3.5 and 2.1 µg/L, respectively. In contrast, the levels of IGFBP-1 measured by ELISA-1–3 in amniotic fluids (AF, n=10) and cerebrospinal fluids (CSF, n=9) were relatively similar (Table 3).

TABLE 3

IGFBP-1 Levels (µg/L) in Physiological Fluids[a]

| Sample | ELISA | Mean | Median | SDE | Range | n | Ratio[b] |
|---|---|---|---|---|---|---|---|
| Serum | 1 | 39.0 | 26.0 | 5.0 | 1.2–127 | 44 | 1.0 |
|  | 2 | 12.9 | 7.8 | 2.0 | 0.1–68 | 44 | 3.3 |
|  | 3 | 2.74 | 2.0 | 0.39 | 0.08–13 | 43 | 13.0 |
| SF | 1 | 18.5 | 19.2 | 5.1 | 2.4–35 | 6 | 1.0 |
|  | 2 | 5.7 | 3.5 | 2.6 | 0.99–18 | 6 | 5.5 |
|  | 3 | 2.8 | 2.1 | 1.1 | 0.04–7.5 | 6 | 9.1 |
| AF | 1 | 10.7 | 8.2 | 2.7 | 1.7–24 | 10 | 1.0 |
|  | 2 | 8.3 | 6.5 | 1.9 | 1.9–18.0 | 10 | 1.26 |
|  | 3 | 10.2 | 7.4 | 2.6 | 1.7–22.8 | 10 | 1.11 |
| CSF | 1 | 6.6 | 3.3 | 2.8 | 0.3–25 | 9 | 1.0 |
|  | 2 | 6.6 | 2.7 | 3.0 | 0.22–27 | 9 | 1.2 |
|  | 3 | 4.7 | 1.9 | 2.1 | 0.13–18.4 | 9 | 1.7 |

[a]Serum samples were selected to fall within the measurement range of all three assays.
AF = Amniotic fluid, diluted 10,000–20,000-fold before testing. CSF = Cerebrospinal fluid.
SF = Synovial Fluid. SDE = standard error of the mean.
[b]Ratio of the median values obtained by ELISA 1 relative to those by ELISA 2 and 3.

Example 4: Effect of IGFBP-1 Dephosphorylation

Dephosphorylation of IGFBP-1 can be readily achieved by sample pre-treatment with alkaline phosphatase (ALP) (Frost, RA et al. J Biol Chem 266:18082–18088, 1991). To investigate whether the apparent method-dependent discrepancy in IGFBP-1 measurement was due to differential antibody recognition of the IGFBP-1 variants, the effect of IGFBP-1 dephosphorylation on the response of ELISA-1–3 was examined.

Seven serum samples (200 uL) were incubated for 2 hrs at room temperature with increasing concentrations of ALP (from 0 to 100 units). The enzyme treated and untreated samples were then analyzed by ELISA- 1–3. As represented in FIG. 5, there was no significant differences in the mean concentration of IGFBP-1 measured by ELISA -1 before and after ALP treatment, suggesting equivalent recognition of all IGFBP-1 variants (non-phosphorylated and phosphorylated variants) by this assay. However, levels detected by ELISA-2 and ELISA-3 increased rapidly in response to increasing levels of ALP treatment and reached a plateau at concentrations close to the level measured by ELISA-1. In this and subsequent experiments, ELISA 3 initially detected only 5–10% of IGFBP-1 measured by ELISA-1 but almost 80% of the total levels after IGFBP-1 dephosphorylation. The reason that the values by ELISA-3 never reached those measured by ELISA-1 may be due to incomplete dephosphorylation of IGFBP-1 or inability of ELISA-3 to recognize certain IGFBP-1 variants. The values by ELISA-2, were consistently higher than those measured by ELISA-3 in untreated samples, but did not show the same level of increase as in ELISA-3 in response to IGFBP-1 dephosphorylation. It is not clear whether the observed IGF-1 interferences in ELISA-2 (Table 1) had further complicated IGFBP-1 measurement by this method. Analysis of 100-1000 units of ALP added to IGFBP- 1 standards did not show any cross-reactivity or interferences in ELISA-1–3.

Figure 6:
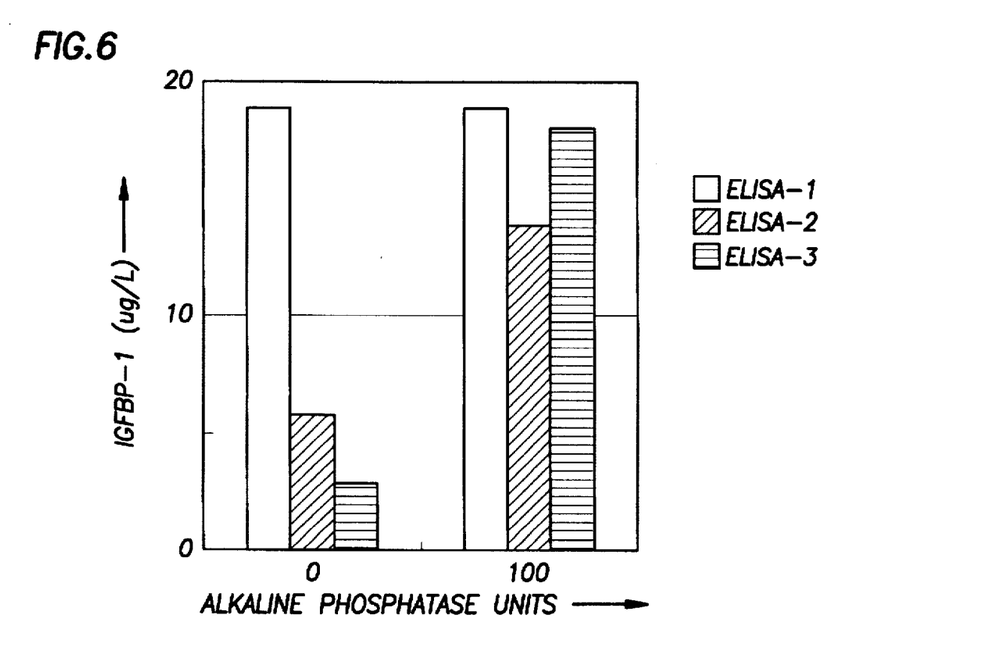
FIG. 6. IGFBP-1 in SF Before and After Dephosphorylation. Open bars represent ELISA- 1, blackened bars represent ELISA-2, and hatched bars represent ELISA-3.

To further evaluate the differential antibody recognition of IGFBP-1 by ELISA-1–3, SF, AF and CSF samples were treated for 2 hours at room temperature with ALP (at 0 and 100 units/200 uL) as above and assayed. As shown in FIG. 6, the pattern of IGFBP-1 immunoreactivity detected in SF by the three ELISAs was similar to that described in experiment 1 for serum samples. ELISA-1 appeared to quantify total IGFBP-1 levels as there was no change in the mean values (n=6) before and after ALP treatment. IGFBP-1 measured by ELISA-2 and ELISA-3 increased significantly in response to ALP treatment, with levels measured by ELISA-3 approaching those detected by ELISA-1.

Figure 7A:
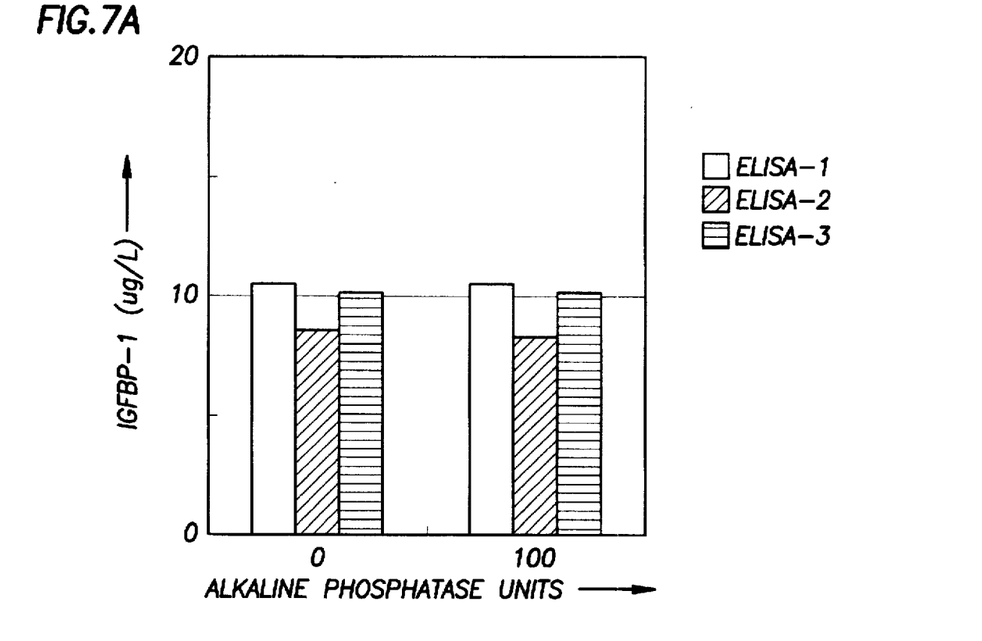
Figure 7B:
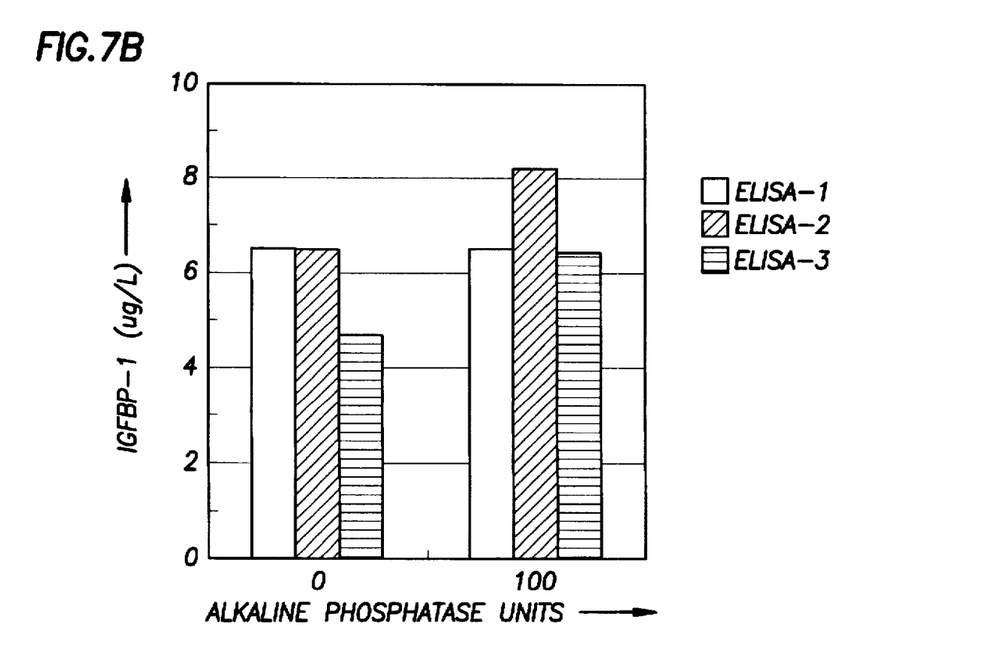

In contrast, the mean IGFBP-1 levels measured in AF (n=10) by ELISA- 1–3 were similar and did not show any significant increases in response to ALP treatment (FIG. 7A, untreated, 0 units ALP; FIG. 7B, treated, 100 units ALP). Similarly, the IGFBP-1 levels in CSF (n=9) demonstrated a relatively smaller response to ALP treatment as measured by ELISA- 1–3. Again, the mean IGFBP-1 values measured by ELISA-1 before and after treatment with ALP were identical. Post-ALP treatment values by ELISA-3 increased, approaching levels detected by ELISA-1, but ELISA-2 appeared to measure a higher IGFBP-1 levels after ALP treatment (FIG. 7B).

To confirm that phosphorylation of IGFBP-1 was responsible for the significantly lower IGFBP-1 levels measured by ELISA-2 and- 3 as well as the scattering of values around the regression line in comparison with ELISA- 1, fresh serum samples (n=21) were treated with ALP (100 units/200 uL) and then assayed.

Figure 8:
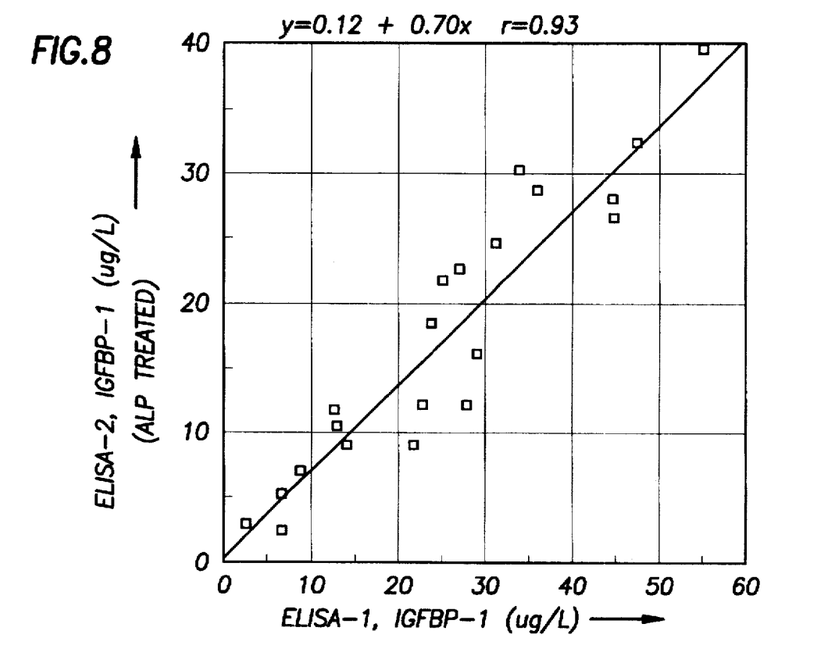
FIG. 8. Comparison of ELISA-1 with ELISA-2 After ALP Treatment.
Figure 9:
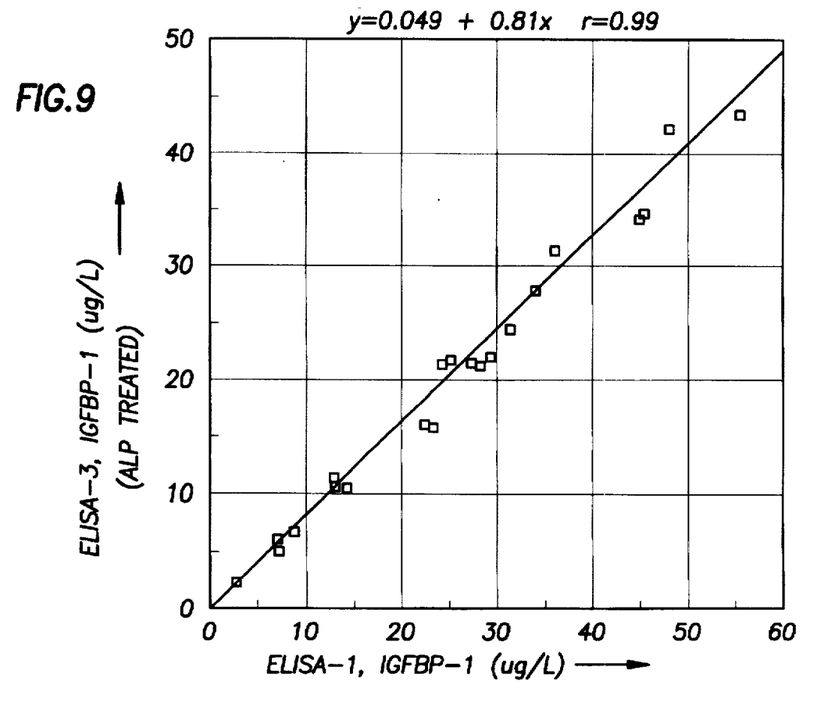
FIG. 9. Comparison of ELISA-1 with ELISA-3 After ALP Treatment.
Figure 10:
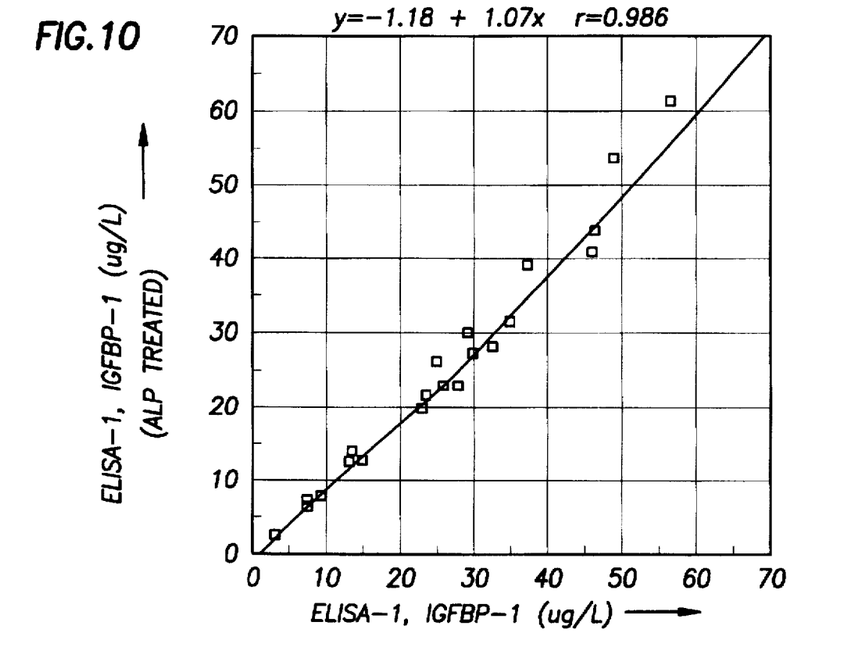
FIG. 10. Comparison of Serum IGFBP-1 values by ELISA-1.

Regression analysis of data showed excellent correlation between IGFBP-1 levels measured by ELISA- 1 in untreated samples in comparison to the corresponding values obtained by ELISA-2 (FIG. 8) and ELISA-3 (FIG. 9) after ALP treatment. As expected, the IGFBP-1 levels by ELISA-2 and ELISA-3 in the treated samples increased to within ~70–80% of those measured by ELISA-1. Similar to the previous observations, ALP treatment had no significant effect on IGFBP-1 measurement by ELISA-1 (FIG. 10). Comparison of values obtained in untreated samples by ELISA-2 and ELISA-3 demonstrated similar levels of IGFBP-1 underestimation and scattering in comparison to ELISA-1 as previously observed in FIG. 4.

Example 5: Comparison to Commercial IGFBP-1 IRMA

Results of a number of experiments clearly indicate that ELISA- 1 is capable of measuring total IGFBP-1 in serum and other biological fluids without being affected by the status of IGFBP-1 phosphorylation. To reemphasize these findings, ELISA-1 was compared to a commercially available IGFBP-1 IRMA (DSL, Inc, Webster, Tex. For this assay, standards or serum samples (0.1 mL) were added to assay tubes precoated with an anti-IGFBP-1 antibody followed immediately by addition of [$^{125}$I]anti-IGFBP-1 recognizing a different epitope(s). The mixture was incubated at room temperature for 16–20 hr, washed and counted (LKB 1275 Minigamma counter, Pharmacia LKB Biotechnology AB, Uppsala, Sweden). Standards ranged from 0.8 to 200 μg/L. Intra- and inter-assay CVs were ~3.4 to 6% within the assay range. The assay had no cross-reactivity with other human IGFBPs.

Figure 11:
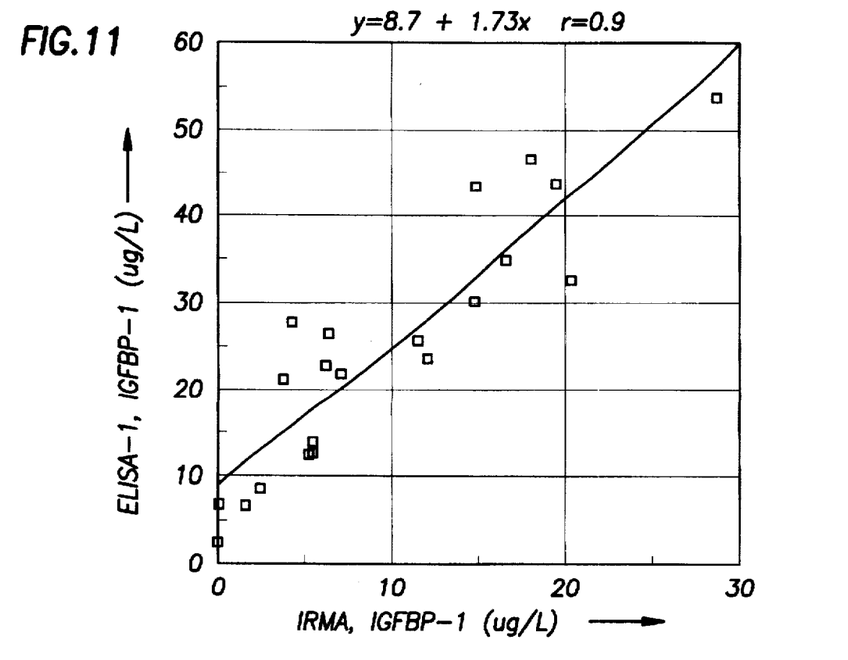
FIG. 11. Comparison of ELISA- 1 with IRMA.
Figure 12:
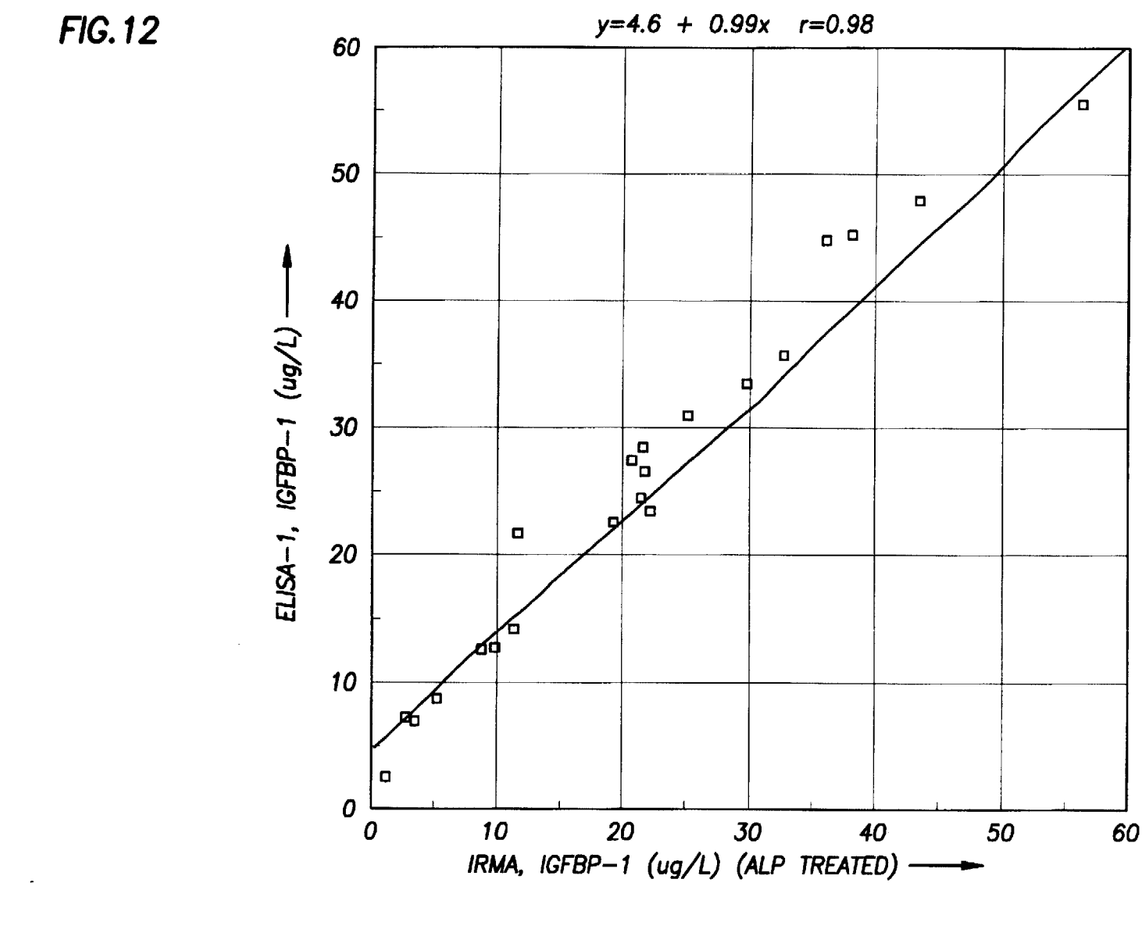
FIG. 12. Comparison of ELISA- 1 with IRMA After ALP Treatment.

Samples (n=2 1) before and after ALP treatments were analyzed by both methods. Regression analysis showed -2- to 3-fold higher IGFBP-1 levels by ELISA-1, with significant scattering of values, in comparison to those measured by the IGFBP-1 IRMA (FIG. 11 ). However, the correlation parameters improved significantly when the IGFBP-1 levels of untreated samples by ELISA-1 were compared to the levels in ALP-treated samples detected by the IRMA (FIG. 12).

Measurement of subsets of IGFBP-1 (e.g. non and lesser phosphorylated forms) is also of value in investigations of their origin or the mechanism that regulates them. Finally, the ability to determine quantitative changes in the levels of the IGFBP-1 subsets relative to its total concentrations allows a more precise definition of the physiological functions and potential diagnostic values of this important binding protein.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. An immunoassay method for the detection of total insulin-like growth factor binding protein- 1 in a fluid comprising the steps of:

a) contacting a sample of fluid suspected of containing insulin-like growth factor binding protein-1 with a first capture antibody that binds to total insulin-like growth factor binding protein-1 to form a complex, wherein said first capture antibody is unaffected by the degree of phosphorylation of insulin-like growth factor binding protein-1, and wherein said first capture antibody is bound to a solid carrier, said solid carrier being insoluble in said fluid;

b) contacting the complex with a second detecting antibody, wherein said second detecting antibody is unaffected by the degree of phosphorylation of insulin-like growth factor binding protein-1 and wherein said second detecting antibody is labeled;

c) separating said solid carrier from said fluid sample and unreacted second detecting antibody;

d) measuring either the amount of labeled second detecting antibody associated with the solid carrier or the amount of unreacted labeled second detecting antibody; and e) relating the amount of labeled antibody measured with the amount of labeled antibody measured for a control sample prepared in accordance with steps (a)–(d), said control sample being known to be free of insulin-like growth factor binding protein, to determine the presence of total insulin-like growth factor binding protein in said fluid sample, or relating the amount of labeled antibody measured with the amount of labeled antibody measured for samples containing known amounts of insulin-like growth factor binding protein prepared in accordance with steps (a)–(d) to determine the concentration of total insulin-like growth factor binding protein in said fluid sample.

2. The method of claim 1 wherein said sample of fluid is a body fluid selected from the group consisting of whole blood, lymphatic fluid, serum, plasma, saliva, amniotic fluid, cerebrospinal fluid, tissue culture media and urine.

3. The method of claim 1 wherein said label is an enzymatic label.

4. The method of claim 3 wherein said enzymatic label is selected from the group consisting of alkaline phospatase, amylase, luciferase, catalase, beta-galactosidase, glucose oxidase, glucose-6-phosphate dehydrogenase, hexokinase, horseradish peroxidase, lactamase, urease and malate dehydrogenase.

5. The method of claim 1 wherein said label is a radioisotope.

6. The method of claim 5 wherein said radioisotope is selected from the group consisting of $^{125}$I, $^{131}$I, $^{32}$P, $^{4}$C, and $^{3}$H.

7. The method of claim 1 wherein said label is a fluorophore.

8. The method of claim 7 wherein said fluorophore is selected from the group consisting of coumarine, rare earth metal ions, chelates or chelate complexes, fluorescein, rhodamine or rhodamine derivatives.

9. The method of claim 1 wherein said label is selected from the group consisting of metal complexes, stable free radicals, vesicles, liposomes, colloidal particles, latex particles, spin labels, biotin/avidin and their derivatives.

10. An immunoassay method for the detection of phosphorylated insulin-like growth factor binding protein-1 in a fluid comprising the steps of:

a) contacting a sample of fluid suspected of containing insulin-like growth factor binding protein-1 with a first capture antibody that binds to total insulin-like growth factor binding protein-1 to form a complex, wherein said first capture antibody is unaffected by the degree of phosphoylation of insulin-like growth factor binding protein-1, and wherein said first capture antibody is bound to a solid carrier, said solid carrier being insoluble in said fluid;

b) contacting the complex with a detecting antibody wherein said detecting antibody binds to non-phosphorylated insulin-like growth factor binding protein-1 and wherein said detecting antibody is labeled;

c) separating said solid carrier from said fluid sample and unreacted detecting antibody;

d) measuring either the amount of labeled detecting antibody associated with the solid carrier or the amount of unreacted labeled detecting antibody;

e) relating the amount of labeled antibody measured with the amount of labeled antibody measured for a control sample prepared in accordance with steps (a)–(d), said control sample being known to be free of said non-phosphorylated insulin-like growth factor binding protein, to determine the presence of non-phosphorylated insulin-like growth factor binding protein in said fluid sample, or relating the amount of labeled antibody measured with the amount of labeled antibody measured for samples containing known amounts of non-phosphorylated insulin-like growth factor binding protein prepared in accordance with steps (a)–(d) to determine the concentration of non-phosphorylated insulin-like growth factor binding protein in said fluid sample; and f) calculating the difference between the total insulin-like growth factor binding protein-1 concentration as determined in claim 1 and the non-phosphorylated insulin-like growth factor binding protein as determined in step (e) to derive the concentration of phosphorylated insulin-like growth factor binding protein-1.

11. The method of claim 10 wherein said sample of fluid is a body fluid selected from the group consisting of whole blood, lymphatic fluid, serum, plasma, saliva, amniotic fluid, cerebrospinal fluid, tissue culture media and urine.

12. The method of claim 10 wherein said label is an enzymatic label.

13. The method of claim 12 wherein said enzymatic label is selected from the group consisting of alkaline phospatase, amylase, luciferase, catalase, beta-galactosidase, glucose oxidase, glucose-6-phosphate dehydrogenase, hexokinase, horseradish peroxidase, lactamase, urease and malate dehydrogenase.

14. The method of claim 10 wherein said label is a radioisotope.

15. The method of claim 14 wherein said radioisotope is selected from the group consisting of $^{125}$I, $^{131}$I, $^{32}$P, $^{14}$C, and $^{3}$H.

16. The method of claim 10 wherein said label is a fluorophore.

17. A kit for measuring total insulin-like growth factor binding protein-1 comprising a first capture antibody that binds to insulin-like growth factor binding protein-1 wherein said first capture antibody is unaffected by the degree of phosphorylation of insulin-like growth factor binding protein-1, wherein said first capture antibody is linked to a solid support and a second detecting antibody, wherein said second detecting antibody is unaffected by the degree of phosphorylation of insulin-like growth factor binding protein-1, and wherein said second detecting antibody is labeled.

* * * * *

UNITED STATES PATENT AND TRADEMARK OFFICE
CERTIFICATE OF CORRECTION

PATENT NO. : 5,747,273

DATED : May 5, 1998

INVENTOR(S) : M. Javad Khosravi; Jehangir Mistry; Anastasia Diamandi

It is certified that error appears in the above-identified patent and that said Letters Patent is hereby corrected as shown below:

At column 1, line 10, replace "IGFBP-I" with --IGFBP-1--.
At column 1, line 49, replace "IGFBP-I" with --IGFBP-1--.
At column 2, line 2, replace "IGF-1" with --IGF-I--.
At column 2, line 32, replace "protein-i" with --protein-1--.
At column 2, line 34, replace "protein- I" with --protein-1--.
At column 6, line 3, replace "FBP-1" with --IGFBP-1--.
At column 10, line 10, replace "IGF-1" with --IGF-I--.
At column 10, line 12, replace "—8" with --~8--.
At column 10, line 14, replace "(>50 µg.L ) with --(≥ 50 µg.L)--.
At column 10, line 16, replace "IGF-1" with --IGF-I--.
At column 10, line 16, replace ">5 µg/L" with --≥5 µg/L--.
At column 10, line 18, replace "IGF-1" with "IGF-I".
At column 10, line 20, replace "(>10 µg/L) with --(≥10 µg/L)--
At column 11, line 25, replace "IGF-1" with --IGF-I--.
At column 14, line 4 replace "n=2 1" with --n=21--.

In the claims:

At column 15, line 2 please delete "tissue culture media".
At column 15, line 14, please replace "$^{32}$p, $^4$C" with --$^{32}$P, $^{14}$C--.
At column 15, line 34, please replace "phosphoylation" with --phosphorylation--.
At column 16, line 23, please delete "tissue culture media".

Signed and Sealed this

Sixth Day of October, 1998

Attest:

BRUCE LEHMAN

Attesting Officer     Commissioner of Patents and Trademarks